US00PP20631P2

(12) United States Plant Patent
De Jong

(10) Patent No.: US PP20,631 P2
(45) Date of Patent: Jan. 5, 2010

(54) ***HYPERICUM* PLANT NAMED 'KOLMAWHI'**

(50) Latin Name: *Hypericum×inodorum*
Varietal Denomination: Kolmawhi

(75) Inventor: Jan De Jong, Heelsum (NL)

(73) Assignee: Kolster Beheer B.V., Bookoop (NL)

( * ) Notice: Subject to any disclaimer, the term of this patent is extended or adjusted under 35 U.S.C. 154(b) by 0 days.

(21) Appl. No.: 12/228,273

(22) Filed: Aug. 11, 2008

(51) Int. Cl.
*A01H 5/00* (2006.01)

(52) U.S. Cl. ..... Plt./442

(58) Field of Classification Search ..... Plt./442, Plt./226

See application file for complete search history.

(56) References Cited

OTHER PUBLICATIONS

UPOV-ROM GTITM, Plant Variety Database 2009/01, GTI Jouve Retrieval Software, Citation for *Hypericum* 'Kolmawhi' one page.*

* cited by examiner

*Primary Examiner*—David H Kruse
*Assistant Examiner*—June Hwu
(74) *Attorney, Agent, or Firm*—C. A. Whealy

(57) ABSTRACT

A new and distinct cultivar of *Hypericum* plant named 'Kolmawhi', characterized by its upright and columnar plant habit; moderately vigorous growth habit; dark green-colored leaves; uniform and freely flowering habit; uniform and high density of fruits; pale yellow-colored fruits; and resistance to *Puccinia* rust.

3 Drawing Sheets

Botanical designation: *Hypericum×inodorum.*
Cultivar denomination: 'Kolmawhi'.

BACKGROUND OF THE INVENTION

The present invention relates to a new and distinct cultivar of *Hypericum*, botanically known as *Hypericum×inodorum* and hereinafter referred to by the name 'Kolmawhi'.

The new *Hypericum* plant is a product of a planned breeding program conducted by the Inventor in Heelsum, The Netherlands. The objective of the breeding program is to create new *Hypericum* cultivars with strong foliage and numerous attractive fruits.

The new *Hypericum* plant originated from a cross-pollination in 2003 in Heelsum, The Netherlands of a proprietary selection of *Hypericum×inodorum* identified as code number 84-2, not patented, as the female, or seed parent with a proprietary selection of *Hypericum×inodorum* identified as code number 88-5, not patented, as the male, or pollen, parent. The new *Hypericum* was discovered and selected by the Inventor as a single flowering plant within the progeny of the stated cross-pollination in a controlled greenhouse environment in Heelsum, The Netherlands in 2005.

Asexual reproduction of the new *Hypericum* plant by vegetative cuttings in Boskoop, The Netherlands since 2006 has shown that the unique features of this new *Hypericum* plant are stable and reproduced true to type in successive generations.

SUMMARY OF THE INVENTION

Plants of the new *Hypericum* have not been observed under all possible environmental conditions. The phenotype may vary somewhat with variations in environment such as temperature and light intensity without, however, any variance in genotype.

The following traits have been repeatedly observed and are determined to be the unique characteristics of 'Kolmawhi'.

These characteristics in combination distinguish 'Kolmawhi' as a new and distinct cultivar of *Hypericum:*

1. Upright and columnar plant habit.
2. Moderately vigorous growth habit.
3. Dark green-colored leaves.
4. Uniform and freely flowering habit; uniform and high density of fruits.
5. Pale yellow-colored fruits.
6. Resistant to *Puccinia* rust.

Plants of the new *Hypericum* differ from plants of the female parent selection in the following characteristics:

1. Plants of the new *Hypericum* have stronger stems than plants of the female parent selection.
2. Plants of the new *Hypericum* are more freely flowering than plants of the female parent selection.
3. Plants of the new *Hypericum* and the female parent selection differ in fruit color as plants of the female parent selection have cream-colored fruits.

Plants of the new *Hypericum* differ from plants of the male parent selection in the following characteristics:

1. Plants of the new *Hypericum* have darker green-colored leaves than plants of the male parent selection.
2. Plants of the new *Hypericum* and the male parent selection differ in fruit color as plants of the male parent selection have pale green-colored fruits.
3. Plants of the new *Hypericum* are resistant to *Puccinia* rust whereas plants of the male parent selection are susceptible to *Puccinia* rust.

Plants of the new *Hypericum* can be compared to plants of the *Hypericum* 'White Condor', not patented. In side-by-side comparisons, conducted in Boskoop, The Netherlands, plants of the new *Hypericum* differed from plants of 'White Condor' in the following characteristics:

1. Plants of the new *Hypericum* were more vigorous than plants of 'white Condor'.
2. Plants of the new *Hypericum* were more uniform than plants of 'White Condor'.

3. Plants of the new *Hypericum* and 'White Condor' differed in fruit color as plants of 'White Condor' had cream-colored fruits.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Hypericum*.

The photograph on the first sheet comprises a top perspective view of a typical flowering plant of 'Kolmawhi'.

The photograph at the top of the second sheet is a close-up view of a typical flower with developing fruit of 'Kolmawhi'; the photograph at the bottom of the second sheet is a close-up view of a typical leaf of 'Kolmawhi'.

The photograph on the third sheet is a close-up view of a typical fruit of 'Kolmawhi'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown for two years under conditions which closely approximate commercial *Hypericum* production conditions in an outdoor nursery in Boskoop, The Netherlands. During the production of the plants, day temperatures ranged from 12° C. to 30° C. and night temperatures ranged from 5° C. to averaged 16° C.

Botanical classification: *Hypericum×inodorum* 'Kolmawhi'.

Parentage:

*Female, or seed, parent.*—Proprietary selection of *Hypericum×inodorum* identified as code number 84-2, not patented.

*Male, or pollen, parent.*—Proprietary selection of *Hypericum×inodorum* identified as code number 88-5, not patented.

Propagation:

*Type cutting.*—Vegetative cuttings.

*Time to initiate roots.*—About three weeks at 18° C. to 30° C.

*Time to produce a rooted young plant.*—About five weeks at 18° C. to 30° C.

*Root description.*—Medium in thickness; fibrous; white in color.

*Rooting habit.*—Moderately freely branching; moderately dense.

Plant description:

*Form.*—Perennial shrub. Columnar plant habit; moderately vigorous growth habit; freely basally branching habit with about 13 flowering stems developing per plant per year; pinching enhances lateral branch development.

*Plant height.*—About 48 cm.

*Plant width (spread).*—About 48.5 cm.

*Lateral branch description.*—Length: About 23.6 cm. Diameter: About 3 mm. Internode length: About 4.2 cm. Strength: Moderately strong. Texture: Smooth, glabrous. Color: Close to 145A to 145B tinged with close to 181A; older stems, close to N199C to N199D.

Foliage description:

*Arrangement.*—Opposite, simple.

*Length.*—About 6.6 cm.

*Width.*—About 4.1 cm.

*Shape.*—Ovate.

*Apex.*—Obtuse.

*Base.*—Truncate.

*Margin.*—Entire.

*Texture, upper and lower surfaces.*—Smooth, glabrous; rugose.

*Venation pattern.*—Pinnate.

*Color.*—Developing leaves, upper surface: Between 143A and 144A. Developing leaves, lower surface: Close to 146C. Fully expanded leaves, upper surface: Darker than 137A; venation, close to 144B to 144C. Fully expanded leaves, lower surface: Between 144B and 146C; venation, close to 144A to 144B.

*Petiole.*—Length: About 1 mm. Diameter: About 4 mm. Texture, upper and lower surfaces: Smooth, glabrous. Color, upper and lower surfaces: Close to 144A.

Flower description:

*Flower arrangement and shape.*—Bright yellow-colored single flowers arranged in terminal compound umbels; freely flowering habit with about twelve flowers per umbel. Flowers face mostly upright.

*Fragrance.*—None detected.

*Natural flowering season.*—During July and August in The Netherlands.

*Flower longevity.*—Flowers last about two or three days on the plant. Flowers not persistent.

*Flower buds.*—Length: About 9 mm. Diameter: About 7 mm. Shape: Broadly ovate. Color: Close to 7B flushed with close to 13A.

*Inflorescence size.*—Height: About 4.5 cm. Diameter: About 7.1 cm.

*Flowers.*—Diameter: About 2.9 cm. Depth (height): About 1.7 cm.

*Petals.*—Quantity/arrangement: Five in a single whorl. Length: About 1.5 cm. Width: About 9 mm. Shape: Obovate. Apex: Obtuse. Base: Attenuate. Margin: Entire. Texture, upper and lower surfaces: Glabrous, smooth. Aspect: Concave. Color, when opening and fully opened, upper and lower surfaces: Close to 12A; color becoming closer to 13A with development.

*Sepals.*—Quantity/arrangement: Five in a single whorl. Length: About 1.3 cm. Width: About 9 mm. Shape: Ovate to broadly ovate. Apex: Obtuse. Base: Broadly cuneate. Margin: Entire. Texture, upper and lower surfaces: Glabrous, smooth. Color: When opening and fully opened, upper surface: Close to 143A. When opening and fully opened, lower surface: Close to 144B.

*Peduncles.*—Strength: Moderately strong. Length: About 2.2 cm. Diameter: About 1.5 mm. Texture: Smooth, glabrous. Color: Close to 144B to 144C.

*Pedicels.*—Strength: Moderately strong. Length: About 1 cm. Diameter: About 1 mm. Aspect: About 40° from the stem axis. Texture: Smooth, glabrous. Color: Close to 143B.

*Reproductive organs.*—Stamens: Quantity per flower: About 100. Filament length: About 1.1 cm. Filament color: Close to 12A. Anther shape: Broadly oval. Anther length: About 0.5 mm. Anther color: Close to 17A. Pollen amount: Scarce. Pollen color: Close to 17A to 17B. Pistils: Quantity per flower: Single pistil with three stigmas. Pistil length: About 5 mm. Stigma shape: Club-shaped. Stigma color: Close to 28B. Style length: About 4.5 mm. Style color: Close to 151C to 151D. Ovary color: Close to 3C to 3D.

*Fruits.*—Length: About 8 mm Diameter: About 9 mm. Shape: Roughly spherical. Texture: Smooth, glabrous. Color: Close to 4C; towards the base, close to 4D.

*Seeds.*—Length: About 0.8 mm. Diameter: About 0.5 mm. Color: Between 199A and N199A.

Disease/pest resistance: Plants of the new *Hypericum* have been noted to be resistant to *Puccinia* rust. Plants of the new *Hypericum* have not been observed to be resistant to pests and other pathogens common to *Hypericum*.

Weather/temperature tolerance: Plants of the new *Hypericum* have been observed to tolerate wind, rain and temperatures ranging from about −20° C. to about 30° C.

It is claimed:

1. A new and distinct *Hypericum* plant named 'Kolmawhi' as illustrated and described.

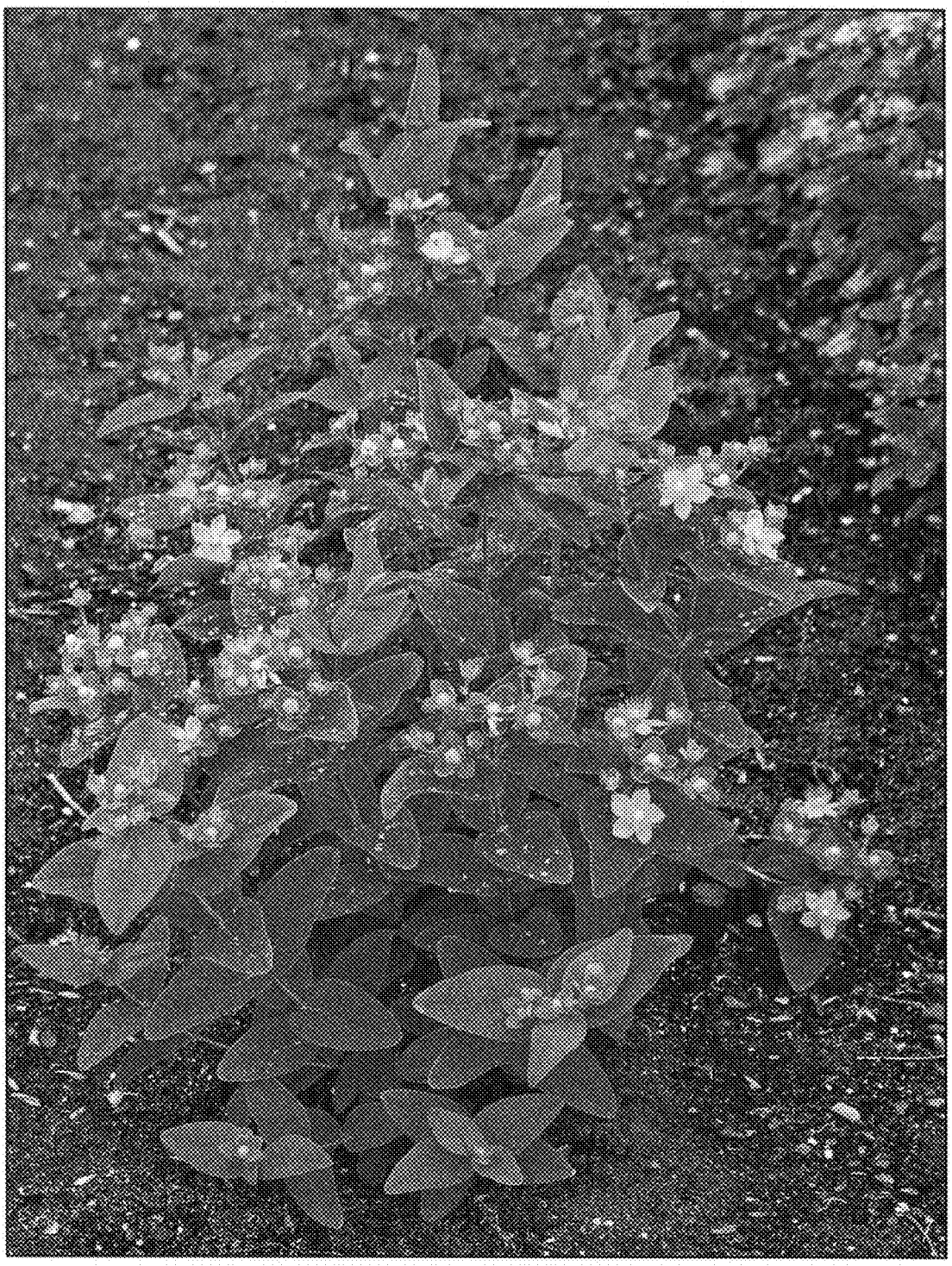

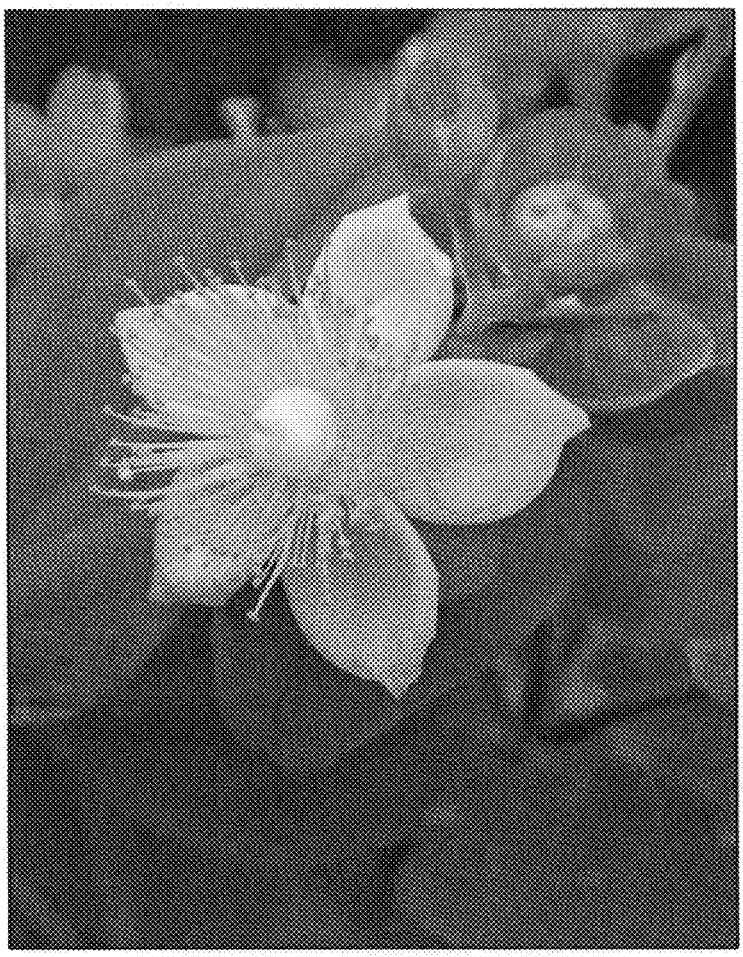
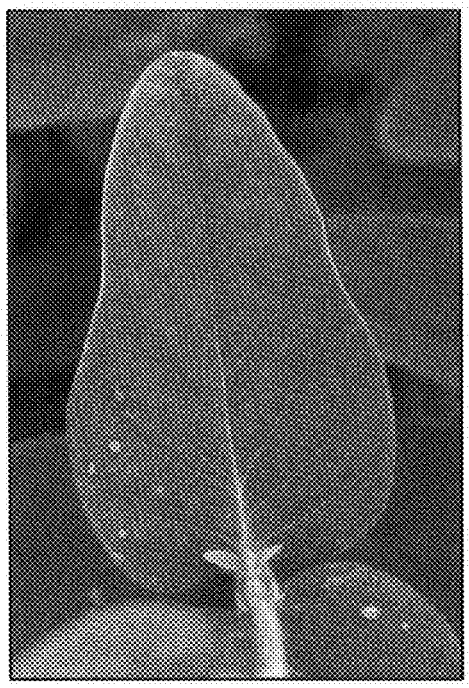

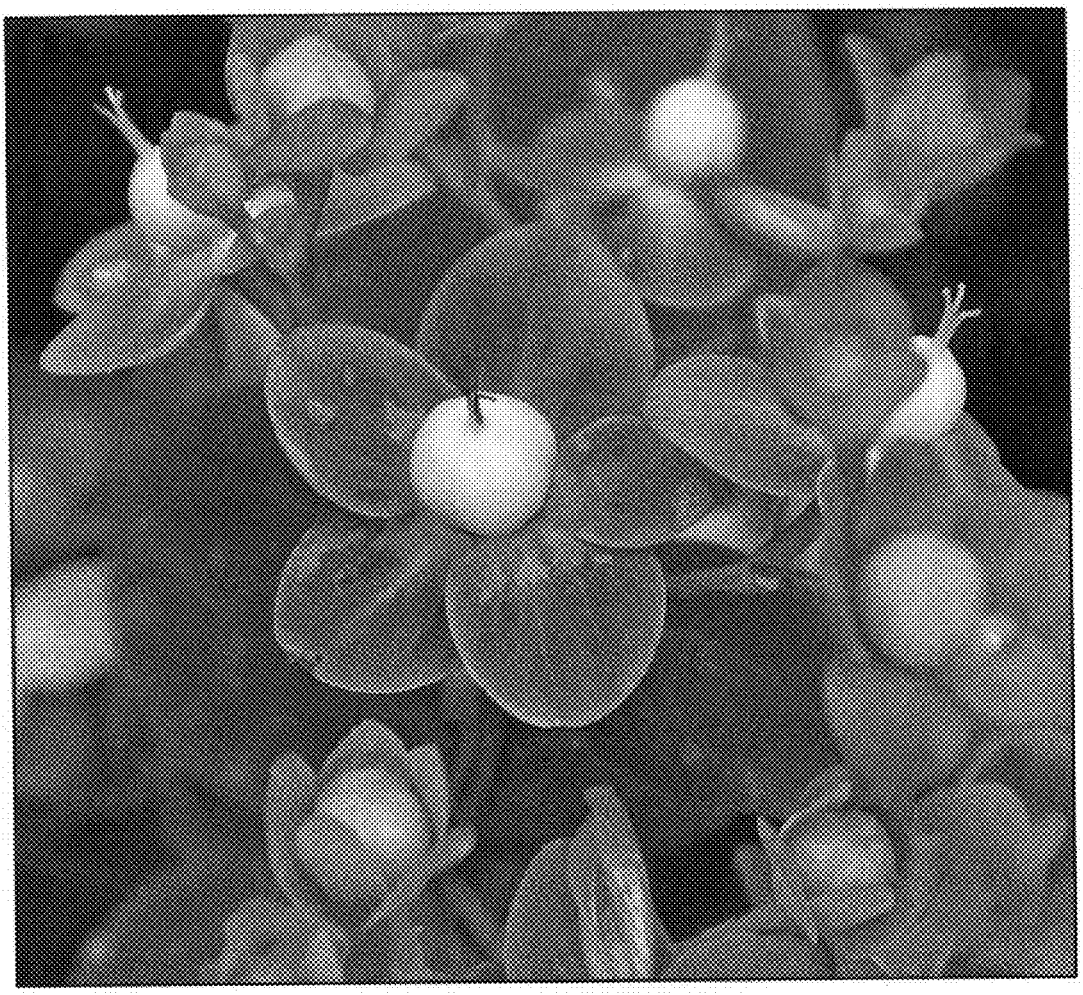

* * * * *